United States Patent [19]

Marecki et al.

[11] Patent Number: 4,655,768

[45] Date of Patent: Apr. 7, 1987

[54] BANDAGE FOR SUSTAINED DELIVERY OF DRUGS

[75] Inventors: Nelda M. Marecki, Plainfield, N.J.; Gary A. Avalon, Painesville, Ohio

[73] Assignee: Avery International Corporation, Pasadena, Calif.

[21] Appl. No.: 788,086

[22] Filed: Oct. 15, 1985

Related U.S. Application Data

[63] Continuation of Ser. No. 628,577, Jul. 6, 1984, abandoned.

[51] Int. Cl.$^4$ ............................................. A61K 9/00
[52] U.S. Cl. ................................. 604/897; 604/307; 128/155; 514/947
[58] Field of Search ............... 604/896, 897, 304, 307, 604/309, 890; 128/155, 156; 424/28, 14

[56] References Cited

U.S. PATENT DOCUMENTS

| | | | |
|---|---|---|---|
| 3,565,075 | 2/1971 | Jerry | 604/307 |
| 3,660,323 | 5/1972 | Raguse | 128/156 |
| 3,964,482 | 6/1976 | Gerstel et al. | 604/896 |
| 3,972,995 | 8/1976 | Tsuk et al. | 128/156 |
| 3,975,570 | 8/1976 | Ono et al. | 128/156 |
| 4,147,831 | 4/1979 | Balinth | 128/156 |
| 4,201,211 | 5/1980 | Chandrasekaran et al. | 604/897 |
| 4,286,592 | 9/1981 | Chandrasekaran et al. | 604/890 |
| 4,307,717 | 12/1981 | Hymes et al. | 128/156 |
| 4,367,732 | 1/1983 | Poulsen et al. | 604/307 |
| 4,486,193 | 12/1984 | Shaw et al. | 604/890 |

Primary Examiner—John D. Yasko
Attorney, Agent, or Firm—Dressler, Goldsmith, Shore, Sutker & Milnamow, Ltd.

[57] ABSTRACT

A bandage for the transdermal or topical administration of a drug over an extended period of time comprising an impermeable backing sheet, a solid drug pellet on the backing sheet, and a layer of contact adhesive covering the pellet and backing sheet. In another form, the adhesive is carried by a web made of a non-woven or woven fabric. Control over the rate of dissolution of the solid drug can be achieved by varying the type of web fabric, the type of adhesive, and the thickness of the adhesive.

30 Claims, 5 Drawing Figures

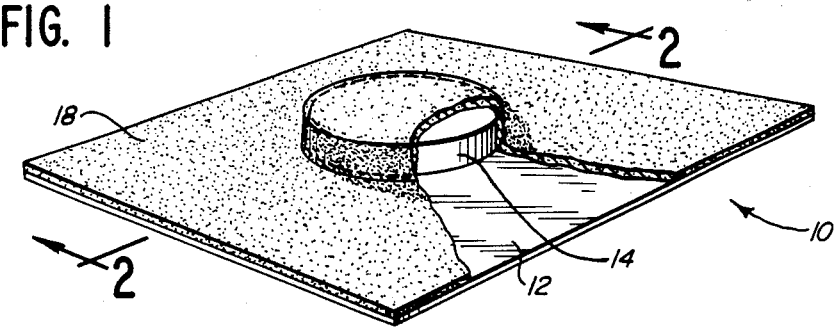
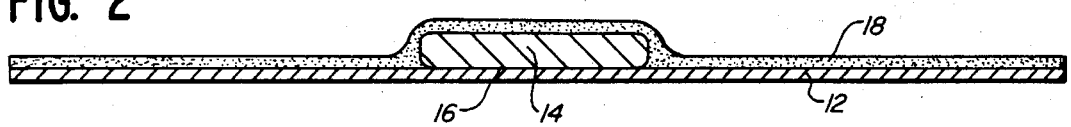
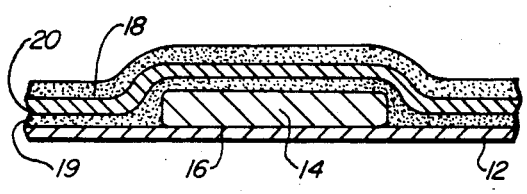
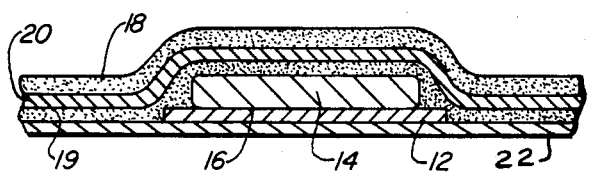
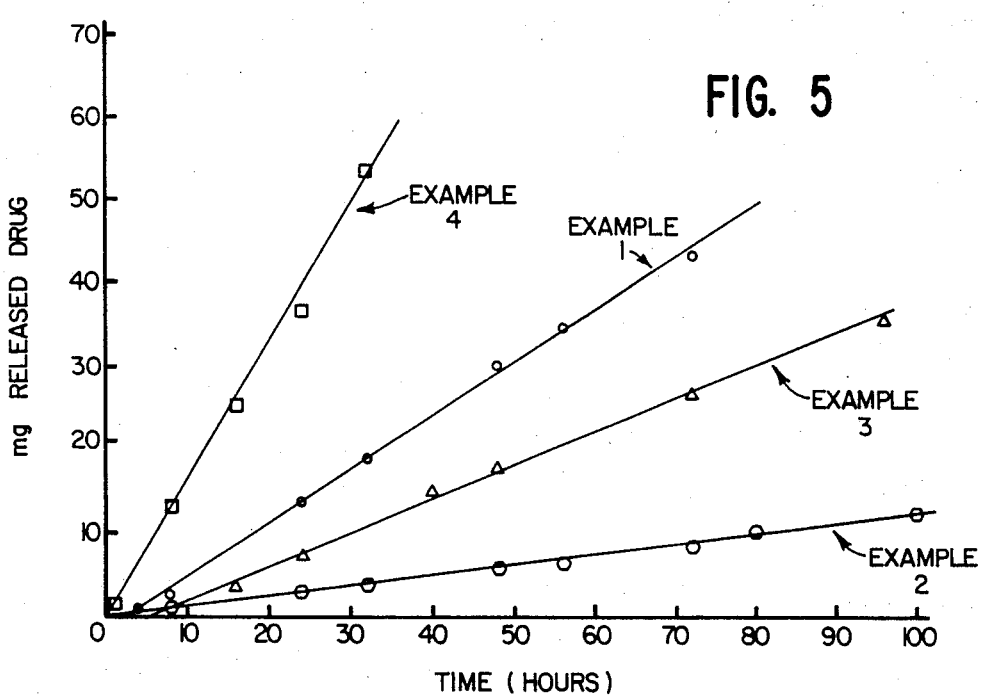

BANDAGE FOR SUSTAINED DELIVERY OF DRUGS

This is a continuation of application Ser. No. 628,577, filed July 6, 1984, now abandoned.

FIELD OF THE INVENTION

This invention relates to bandages and systems for controlled release of transdermally or topically administered drugs and, more particularly, to an improved bandage in which the patient's normal skin moisture effects dissolution and delivery of the drug.

BACKGROUND OF THE INVENTION

As used in this application and the appended claims, the word "drugs" is intended in its broadest sense to apply to all medicaments of any type, whether topical or systemic, applied for therapeutic purposes.

In recent years, there have been provided numerous bandages designed for delivery of drugs to the skin or mucosa of the wearer. One group of such prior bandages is represented by U.S. Pat. Nos. 3,632,740; 3,769,071; and 3,896,789, which teach the incorporation of specific active agents into a pressure sensitive adhesive for direct contact with skin lesions, and the like. Those bandages had no means for control of the rate of delivery and were objectionable for many applications because of the direct contact of the drug with the skin.

Another group of prior bandages employed specially designed diffusion membranes and drug reservoirs as represented by U.S. Pat. Nos. 3,598,122 and 4,069,307. Those bandages were complex, expensive, and involved difficult and precise manufacturing techniques.

An offshoot or refinement of the drug reservoir approach resulted in the micro-encapsulation of fine particles of the drug and the dispersion of the microcapsules within a matrix comprising a discrete layer of a laminar structure. Representative of such bandages are U.S. Pat. Nos. 3,996,934; and 3,598,123. Once again, such bandages were complex, costly and difficult to make.

U.S. Pat. No. 4,286,592 teaches another laminate bandage in which the drug is dispersed in a dissolution carrier matrix, and discusses the use of an adhesive to control the rate of dissolution and administration of the drug. Here, too, the bandage was complex and costly and required specific manufacturing parameters.

A simpler bandage is shown in U.S. Pat. No. 4,307,717, but it still required that the drug be dispersed in a matrix and it did not address the question of control of the rate of dissolution.

SUMMARY OF THE INVENTION

The present invention grows out of the discovery that sustained, substantially constant rate of release over long periods of time can be obtained using drugs in solid form. In its broadest form, the bandage of the invention comprises only a liquid-impermeable backing, a solid drug, preferably in pellet form, and a moisture-permeable skin contact adhesive. Controlled rate dissolution of the solid drug results from contact therewith of water or water vapor emanating from the skin of the wearer.

The solid drug may be used in its pure form and no added excipients, matrices, or dissolution carriers are required. The salutary results achieved derive from the correlation between the body moisture and the solubility of the drug therein and the fact that such moisture can pass through the adhesive up to the drug and the dissolved drug is able to pass back through the adhesive to the skin of the patient.

Further control of the rate of dissolution can be obtained in a number of ways. One method is by varying the composition of the adhesive and/or its thickness. Another method is to incorporate into the adhesive a vehicle in which the drug is soluble, but more or less soluble than in the body moisture of the patient.

The bandage may also include a carrier web for the adhesive. The carrier web material can also be selected so that it may have an effect on the rate of dissolution. In all its forms, the inventive bandage is simple, efficient, inexpensive to make, and eliminates the objectionable features of the prior art devices, such as, drug reservoirs, matrices, microencapsulation, diffusion membranes, and the like.

Other features and advantages of the invention will be apparent from the following description and claims and are illustrated in the accompanying drawings which show structure embodying preferred features of the present invention and the principles thereof.

BRIEF DESCRIPTION OF THE DRAWINGS

FIG. 1 is a perspective view of a bandage embodying the principles of the invention with portions of the adhesive layer being broken away to reveal internal structure;

FIG. 2 is an enlarged vertical sectional view taken on the plane of line 2—2 in FIG. 1;

FIG. 3 is a similar view of a modified form of the bandage;

FIG. 4 is a similar view of another modified form of the bandage; and

FIG. 5 is a graph of the dissolution of two representative drugs plotted against time, the drug for the bandages of Examples 1, 2, and 3 being timolol, and the drug for the bandage of Example 4 being phenylephrine hydrochloride.

DESCRIPTION OF THE PREFERRED EMBODIMENTS OF THE INVENTION

Referring with greater particularlity to the various figures of tne drawings, there is illustrated in FIGS. 1 and 2 the basic bandage structure of the invention indicated generally by the numeral 10. Bandage 10 comprises a flexible liquid-impermeable backing layer or sheet 12. The backing sheet 12 is chosen to prevent migration of the drug therethrough and insure one-way diffusion of the drug when applied. In this regard, the backing sheet may be gas-impermeable as well as liquid-impermeable, it being necessary only that the same be impermeable to the drug in its dissolved or vaporized state. For this purpose, a variety of thin, sheet-like materials are suitable, including aluminum foil, polyester, polypropylene, polyetnylene, polyurethane film, and a laminate of aluminum foil and polyester. Desirably, backing sheet 12 is thin and flexible, having a thickness in the range of 6 to 50 microns.

Positioned on the backing sheet 12 is a thin pellet 14 made of a compressed, solid drug. The solid drug pellet 14 may be substantially circular in form and have an inner face 16 of substantially larger dimensions than the pellet's thickness. In this regard, the pellet 14 may range between 0.5 and 10 cm in diameter, 5 and 1,000 microns in thickness, and have a mass between 1 and 1,000 mg. The significance of the relatively large surface area 16 will become apparent as the description proceeds.

A layer of skin contact adhesive 18 covers the pellet 14 and retains the same on the backing sheet 12. The layer 18 may comprise any of the conventional pressure sensitive adhesives, such as, acrylic copolymer, styrene-butadiene-styrene, styrene-isoprene-styrene and silicone polymer, and may also contain tackifying resins.

The acrylic adhesives may be selected from a variety of pressure-sensitive adhesive copolymers as are well known in the art. Broadly, the useful pressure-sensitive adhesives include the copolymers of acrylic and/or methacrylic acids, alkyl acrylate and methacrylate esters containing 1 to 10 carbon atoms, such as, methyl methacrylate and 2-ethyl-hexyl acrylate, acrylamides and methacrylamides, and additional copolymerizable monoethylenically unsaturated monomers, such as, vinyl acetate, acrylonitrile and alkyl vinyl ethers containing 1 to 10 carbon atoms, such as, propyl vinyl ether.

More specifically, the pressure-sensitive acrylic adhesives may comprise copolymers of 2-ethyl-hexyl acrylate, vinyl acetate and acrylic acid sold under such trademarks or tradenames as Gelva RA-788 made by Monsanto, AS-351 made by Avery Chemical and Aeroset 1085 made by Ashland.

The pressure-sensitive rubber-based adnesives may likewise be selected from a variety of compounds of styrene-butadiene-styrene (SBS) and/or styrene-isoprene-styrene (SIS) block copolymers, one or more plasticizers and a stabilizer. Such pressure-sensitive adhesives may include compounds of rubber-based block copolymers such as Kraton 1101 (SBS) or 1107 (SIS) (Shell Chemical Company), one or more tackifier resins sold under such trademarks or tradenames as Hercolyn D, Piccolyte A-115, Stabilite Ester 10 and Foral 85, and a suitable stabilizer.

More specifically, the pressure-sensitive rubber-based adhesives may comprise from 10 to 30% block copolymers of styrene-butadiene-styrene or styrene-isoprene-styrene, from 30 to 70% tackifying resins and 1 to 3% of a stabilizer.

Silicone adhesives may comprise solvent solutions of silicone gum and resin, partially condensed, of the type sold under such trademarks or tradenames as Dow Corning 355, and PSA 595 or PSA 6574 made by General Electric. PSA 595 is reported to comprise a xylene solution of a reactive copolymer of polydimethylsiloxane gum and polysiloxane resin; and PSA 6574 is reported to comprise a toluene/naphtha solution of a silicone gum containing [(CH$_3$)$_2$SiO] and [(C$_6$H$_5$)$_2$SiO]- groups and a MQ resin, said resin being condensed water glass reacted with trimethylchlorosilane.

Thickness and composition of the adhesive layer 18 has been discovered to have an effect on controlling the rate of dissolution of the drug pellet 14 as will subsequently be described. It has thus been found that acrylic adhesives permit faster rates of dissolution than a rubber-based adhesive, and the adhesives may likewise contain tackifying resins, or other additions or fillers. Adhesive layers between 10 and 150 microns in thickness have been found to be effective depending upon the particular drug and application involved. The adhesive layer 18 may be further modified by addition of a drug dissolution vehicle as will be seen from an example to be described.

Any solid drug which is compressible or handleable in powder form may be employed in its pure form without the addition of any additives. In general, the drug will have a relatively low melting point, on the order of less than 150° C. and be relatively soluble in water, in the range of 0.1 to 100 mg/ml. Successful results have been achieved with adrenergics such as timolol and phenylephrine hydrochloride.

In FIG. 3, there is illustrated a modified form of the bandage 10 wherein the adhesive layer 18 comprises the outer coating of a carrier web 20. As indicated, the carrier web is likewise coated with a layer of adhesive 19 on the inner or pellet side thereof. The adhesive layer 19 may vary in thickness between 20 and 300 microns and may be the same as layer 18, or comprise a different adhesive. Preferably, carrier web 20 comprises a nonwoven fabric composed of nylon, polyethylene, polypropylene, rayon, cellulose-rayon, or polyester and having a fabric weight of from 1 to 100 gm/m$^2$. Woven fabrics of gauze or cellulosic materials having a weight of from 0.5 to 100 gm/m$^2$ may also be employed. Choice of carrier web material can have an effect on the rate of dissolution apparently related to the polarity of the material of construction. It has thus been discovered, for example, that a carrier made of a relatively polar molecule, such as nylon, tends to retard the rate of dissolution.

In FIG. 4, there is illustrated another modified form of the bandage 10. In this embodiment, the impermeable backing sheet 12 is covered by an outer layer 22 to give the bandage a finished feel, look and wearability. The outer layer 22 should be flexible, conformable, lightweight and comfortably wearable. In this regard the outer layer 22 may comprise occlusive films of polyethylene, polypropylene, polyvinyl chloride and polyurethane, or non-occlusive woven or non-woven fabrics of the same composition as the carrier web 18 or a perforated film of any of the listed materials, and ranging in thickness from 10 to 200 microns.

As a final finish, the bandage 10 preferably includes a protective liner (not shown), for example, silicone or polyfluoroethylene coated release liners as are well known in the art, removably adhered to pressure sensitive layer 18. Such a liner may be made of paper or film on the order of 25 to 200 microns thickness and protects the adhesive prior to use and prevents drug migration through the adhesive during storage.

The examples which follow illustrate the invention, but are not intended to limit the invention in any way.

EXAMPLE 1

A bandage for administering the beta-adrenergic blocker timolol transdermally for a period in excess of 80 hours was made in the following manner. A 50 mg wafer-like pellet of timolol was prepared in a standard potassium bromide pellet press, the substantially circular pellet having a diameter of about 1.25 cm and a thickness of about 350 microns. The drug pellet was placed on aluminum foil of 50 microns thickness and this was overlaid with a layer of acrylic adhesive of 50 microns thickness, said adhesive being mass cast from solution (toluene, heptane) at 40–50% solids, wherein the acrylic fraction comprises an acrylic copolymer prepared through reaction of 2-ethyl-hexyl acrylate, vinyl acetate and acrylic acid. In vitro release tests were carried out on the bandage using standard apparatus and techniques, namely Standard U.S.P. Type 2 dissolution apparatus with a phosphate buffer solution of pH 7.4. Constant release of the drug was sustained over a period in excess of 80 hours, after which the release slowed appreciably and the drug was substantially exhausted. Between 4 and 72 hours, the drug release approached a linear rate.

EXAMPLE 2

A bandage for administering timolol was made. As in Example 1, a 50 mg pellet of the drug was prepared and placed on aluminum foil of 50 microns thickness. The pellet was then overlaid with a tackified styrene-butadiene-styrene pressure-sensitive adhesive containing 5% mineral oil, said adhesive being mass cast from solution (toluene, heptane) at 40–50% solids, wherein the rubber fraction comprises a compound of 18% styrene-butadiene-styrene block copolymer, 15% random styrene-butadiene copolymer, 61% tackifying resins, 5% mineral oil, and 1% stabilizer. For purposes of comparison, the solubility of timolol is about 8 mg/ml in water and about 4 mg/ml in mineral oil. In the same standard in vitro release tests substantially constant release of the drug was sustained for a period in excess of 120 hours after which the release slowed appreciably and the drug was substantially exhausted. Between 8 and 100 hours, the drug release approached a linear rate.

EXAMPLE 3

A bandage for the administration of timolol was made by preparing a pellet of the drug and placing the same on aluminum foil as in Examples 1 and 2. The pellet was then overlaid with an adhesive carrier web made of non-woven polyester having a fabric weight of 19.9 gm/m$^2$. The carrier web had previously been coated on the pellet side with acrylic adhesive, having the same composition as in Example 1, of 25 microns thickness and on the non-pellet, or skin-contact, side with the same acrylic adhesive of 50 microns thickness. In the same standard in vitro release tests substantially constant release of the drug was sustained for a period in excess of 120 hours after which the release slowed appreciably and the drug was substantially exhausted. Between about 15 and 96 hours, the drug release approached a linear rate.

EXAMPLE 4

A bandage for tne administration of the drug phenylephrine hydrochloride was made in the following manner. A 70 mg wafer-like pellet of the drug was prepared in a standard potassium bromide pellet press, the substantially circular pellet having a diameter of about 1.25 cm and a tnickness of about 350 microns. The drug pellet was placed on aluminum foil of 50 microns tnickness. This was overlaid with an adhesive carrier web made of a non-woven polyester having a fabric weight of 19.9 gm/m$^2$. The carrier web had previously been coated on the pellet side with tackified styrene-butadiene-styrene pressure-sensitive adhesive, having the same composition as in Example 2, of 25 microns thickness and on the non-pellet, or skin-contact, side with acrylic adhesive, having the same composition as in Example 1, of 50 microns thickness. In the same standard in vitro release tests, substantially constant release of the drug was sustained for a period in excess of 35 hours, after which the drug release slowed appreciably and the drug was substantially exhausted. Between about 1 and 32 hours, the drug release approached a linear rate.

It should be apparent from the foregoing that the invention provides a simple, efficient and inexpensive bandage for the sustained transdermal or topical administration of drugs over an extended period of time. The use of solid drugs advantageously eliminates all matrices, encapsulations and dissolution media of the type heretofore required in bandages of this type. It should be appreciated that the term "bandage" is used in its generic sense to apply to any skin adhesive device whatever its form or shape. While preferred embodiments have been illustrated and described herein, changes and variations may be made by those skilled in the art without departing from the spirit and scope of the appended claims. The invention is defined by the claims that follow.

What is claimed is:

1. A bandage for transdermal or topical administration of a drug to the wearer thereof comprising:
   a liquid-impermeable backing sheet;
   a solid pure drug pellet constituted by compressed solid water-soluble drug powder positioned on said backing sheet;
   a layer of pressure-sensitive adhesive covering said drug pellet and backing sheet so that all upraised surfaces of said pellet are encased by said adhesive and said pellet makes no physical contact with the wearer during administration of the drug, whereby said adhesive remains in physical contact with the wearer and the drug is administered through said adhesive to the wearer's skin.

2. The bandage of claim 1 wherein said backing sheet comprises a material selected from the group consisting of aluminum foil, polyester, polypropylene, polyethylene, polyurethane film, and a laminate of aluminum foil and polyester.

3. The bandage of claim 2 wherein said backing sheet has a thickness between 6 and 50 microns.

4. The bandage of claim 1 wherein said drug pellet is substantially circular in configuration and has a diameter between 0.5 and 10 cm and a thickness between 5 and 1,000 microns.

5. The bandage of claim 4 wherein said drug pellet weighs between 1 and 1,000 mg.

6. The bandage of claim 1 wherein said pressure-sensitive adhesive comprises an adhesive selected from a group consisting of acrylic copolymer, styrene-butadiene-styrene, styrene-isoprene-styrene, and silicone polymer.

7. The bandage of claim 6 wherein said adhesive layer has a thickness between 10 and 150 microns.

8. The bandage of claim 6 wherein said pressure-sensitive adhesive has mineral oil incorporated therein.

9. A bandage for transdermal or topical administration of a drug to the wearer thereof comprising:
   a liquid-impermeable backing sheet;
   a solid pure drug pellet constituted by compressed solid water-soluble drug powder positioned on the inner surface of said backing sheet; and
   a carrier web coated with pressure-sensitive adhesive covering said pellet and backing sheet so that all upraised surfaces of said pellet are encased by said carrier web and said pellet makes no physical contact with the wearer during administration of the drug, whereby said adhesive coated web remains in physical contact with the wearer and the drug is administered through said adhesive to the wearer's skin.

10. The bandage of claim 9 wherein said carrier web comprises a non-woven fabric selected from a group consisting of nylon, polyethylene, polypropylene, rayon, cellulose-rayon, and polyester.

11. The bandage of claim 10 wherein said non-woven fabric has a weight between 1 and 100 mg/m$^2$.

12. The bandage of claim 9 wherein said carrier web comprises a woven fabric of gauze or cellulosic materials having a weight of between 0.5 and 100 gm/m$^2$.

13. The bandage of claim 9 wherein said carrier web is coated with said adhesive on both of its surfaces.

14. The bandage of claim 13 wherein said adhesive comprises an adhesive selected from the group consisting of acrylic copolymer, styrene-butadiene-styrene, styrene-isoprene-styrene, and silicone polymer.

15. The bandage of claim 14 wherein the coating of said adhesive on the skin contact surface of said carrier web has a thickness between 10 and 300 microns and the coating on the inner surface of said web has a thickness of between 10 and 300 microns.

16. The bandage of claim 9 wherein said drug pellet is substantially circular in configuration and has a diameter between 0.5 and 10 cm and a thickness between 5 and 1,000 microns.

17. The bandage of claim 16 wherein said drug pellet weighs between 1 and 1,000 mg.

18. The bandage of claim 15 wherein the adhesive on each of the surfaces of said carrier web comprises acrylic copolymer.

19. The bandage of claim 18 wherein the adhesive coating on the skin contact surface of said carrier web is approximately twice the thickness of the adhesive coating on the inner surface of said web.

20. The bandage of claim 15 wherein the adhesive on the skin contact surface of said carrier web comprises acrylic copolymer and the adhesive on the inner surface of said web comprises styrene-butadiene-styrene.

21. The bandage of claim 20 wherein said acrylate copolymer adhesive coating is approximately twice the thickness of said styrene-butadiene-styrene adhesive coating.

22. The bandage of claim 9 wherein said backing sheet comprises a material selected from the group consisting of aluminum foil, polyester, polypropylene, polyethylene, polyurethane film, and a laminate aluminum foil and polyester.

23. A bandage for transdermal or topical administration of a drug to the wearer thereof comprising:
    a liquid-impermeable backing sheet;
    a layer of pressure-sensitive adhesive covering said backing sheet; and
    a solid pure drug pellet constituted by compressed water-soluble drug powder retained between said backing sheet and adhesive layer and encased by said adhesive so that said drug makes no physical contact with the wearer during administration thereof, whereby said adhesive remains in physical contact with the wearer and the drug is administered through said adhesive to the wearer's skin.

24. The bandage of claim 23 wherein said backing sheet comprises a material selected from the group consisting of aluminum foil, polyester, polypropylene, polyethylene, polyurethane film, and a laminate of aluminum foil and polyeste,r.

25. The bandage of claim 24 wnerein said backing sheet has a thickness between 6 and 50 microns.

26. The bandage of claim 23 wherein said drug pellet is substantially circular in configuration and has a diameter between 0.5 and 10 cm and a thickness between 5 and 1,000 microns.

27. The bandage of claim 26 wherein said drug pellet weighs between 1 and 1,000 mg.

28. The bandage of claim 23 wherein said pressure-sensitive adhesive comprises an adhesive selected from a group consisting of acrylic copolymer, styrene-butadiene-styrene, styrene-isoprene-styrene, and silicone polymer.

29. The bandage of claim 28 wnerein said adhesive layer has a thickness between 10 and 150 microns.

30. The bandage of claim 28 wherein said pressure-sensitive adhesive has mineral oil incorporated therein.

* * * * *